(12) United States Patent
Arnin et al.

(10) Patent No.: US 7,758,647 B2
(45) Date of Patent: Jul. 20, 2010

(54) ELASTOMERIC SPINAL DISC NUCLEUS REPLACEMENT

(75) Inventors: Uri Arnin, Kiryat Tivon (IL); Yuri Sudin, Lod (IL); Michael Tauber, Tel Aviv (IL)

(73) Assignee: Impliant Ltd., Ramat Poleg (IL)

( * ) Notice: Subject to any disclaimer, the term of this patent is extended or adjusted under 35 U.S.C. 154(b) by 38 days.

(21) Appl. No.: 10/565,205

(22) PCT Filed: Jul. 25, 2004

(86) PCT No.: PCT/IL2004/000674

§ 371 (c)(1),
(2), (4) Date: Jan. 20, 2006

(87) PCT Pub. No.: WO2005/009299

PCT Pub. Date: Feb. 3, 2005

(65) Prior Publication Data

US 2006/0190083 A1    Aug. 24, 2006

Related U.S. Application Data

(60) Provisional application No. 60/489,914, filed on Jul. 25, 2003, provisional application No. 60/512,192, filed on Oct. 20, 2003.

(51) Int. Cl.
*A61F 2/46* (2006.01)
(52) U.S. Cl. .................................... 623/17.16
(58) Field of Classification Search ... 623/17.11–17.16; 606/60–63, 72, 192
See application file for complete search history.

(56) References Cited

U.S. PATENT DOCUMENTS

| | | | | |
|---|---|---|---|---|
| 4,969,888 A | * | 11/1990 | Scholten et al. | 606/94 |
| 5,059,193 A | * | 10/1991 | Kuslich | 606/61 |
| 5,108,404 A | * | 4/1992 | Scholten et al. | 606/94 |
| 5,147,370 A | * | 9/1992 | McNamara et al. | 623/1.11 |
| 5,309,896 A | * | 5/1994 | Moll et al. | 600/207 |
| 6,235,028 B1 | * | 5/2001 | Brumfield et al. | 606/53 |
| 6,235,043 B1 | * | 5/2001 | Reiley et al. | 606/192 |
| 6,248,110 B1 | * | 6/2001 | Reiley et al. | 606/93 |
| 6,530,926 B1 | * | 3/2003 | Davison | 606/279 |
| 6,676,665 B2 | * | 1/2004 | Foley et al. | 606/105 |
| 6,706,069 B2 | * | 3/2004 | Berger | 623/17.12 |
| 6,899,719 B2 | * | 5/2005 | Reiley et al. | 606/192 |

(Continued)

FOREIGN PATENT DOCUMENTS

WO    WO 00/44319    8/2000

OTHER PUBLICATIONS

Written Opinion, WO 2005/009299 (PCT/IL2004/000674).

*Primary Examiner*—David J Isabella
*Assistant Examiner*—Ann Schillinger
(74) *Attorney, Agent, or Firm*—Dekel Patent Ltd.; David Klein

(57) ABSTRACT

A spinal disc nucleus replacement including an elastomeric sheath (12) assembled around a rod (14), a portion of the sheath being arranged for sliding along the rod, and a sheath compactor (18) adapted to slide a portion of the sheath along the rod from a first position to a second position, wherein in the first position the sheath is in a non-expanded orientation and in the second position the sheath is in an expanded orientation wherein folds of the sheath expand radially outwards from the rod.

16 Claims, 12 Drawing Sheets

U.S. PATENT DOCUMENTS

| | | | |
|---|---|---|---|
| 6,979,341 B2 * | 12/2005 | Scribner et al. | 606/192 |
| 6,981,981 B2 * | 1/2006 | Reiley et al. | 606/192 |
| 7,044,954 B2 * | 5/2006 | Reiley et al. | 606/93 |
| 7,077,865 B2 * | 7/2006 | Bao et al. | 623/17.12 |
| 7,097,648 B1 * | 8/2006 | Globerman et al. | 606/99 |
| 2002/0016583 A1 * | 2/2002 | Cragg | 604/500 |
| 2002/0026195 A1 * | 2/2002 | Layne et al. | 606/72 |
| 2002/0068974 A1 * | 6/2002 | Kuslich et al. | 623/17.11 |
| 2002/0077701 A1 * | 6/2002 | Kuslich | 623/17.12 |
| 2002/0111685 A1 * | 8/2002 | Ralph et al. | 623/17.13 |
| 2002/0120336 A1 * | 8/2002 | Santilli | 623/17.16 |
| 2002/0147497 A1 * | 10/2002 | Belef et al. | 623/17.12 |
| 2004/0167625 A1 * | 8/2004 | Beyar et al. | 623/11.11 |
| 2005/0143818 A1 * | 6/2005 | Yuan et al. | 623/17.11 |

* cited by examiner

ELASTOMERIC SPINAL DISC NUCLEUS REPLACEMENT

CROSS-REFERENCE TO RELATED APPLICATIONS

This application claims priority under 35 USC §119 to U.S. Provisional Patent Application Ser. No. 60/489,914, filed Jul. 25, 2003, and U.S. Provisional Patent Application Ser. No. 60/512,192, filed on Oct. 20, 2003, which are both incorporated herein by reference.

FIELD OF THE INVENTION

The present invention relates to a prosthetic spinal disc nucleus and, more particularly, to a prosthetic spinal disc nucleus which includes an elastomeric sheath and medial rod. The sleeve bearing sheath may be implanted in a narrow form and subsequently widened by contraction of the sleeve axially upon the rod thereby causing the prosthetic spinal disc nucleus to occupying an increased portion of the volume of an intra-discal space.

BACKGROUND OF THE INVENTION

The intervertebral disc is composed of three distinctively different tissues: annulus fibrosis, nucleus pulposus, and vertebral endplate. Treatment of spinal disc disorders is often attempted by replacement of the disc nucleus (prosthetic nuclear implantation). This procedure is of importance because it can preserve the remaining disc tissues, that is, the annulus and the endplates, and therefore can preserve their functions. The primary objectives of prosthetic nucleus implantation are to re-gain the disc space and to relieve the compressive load on this disc component by sharing a significant portion of that load.

U.S. Pat. No. 5,800,549 to Bao describes implanting one or several (four implants were used in one example) dehydrated prosthetic hydrogel nuclei into the intradiscal space. Subsequent to implantation these implanted nuclei hydrate to a shape conforming to the natural nucleus. Bao also describes an insertion device for inserting an elastic prosthetic spinal nucleus into the intervertebral space. The insertion device includes a force-transmitting element for a rapid deployment of the prosthesis into the disc space in order to prevent permanent deformation of the elastic prosthetic nucleus. These implants taught by Bao are relatively large and have to be compressed in order to pass through the device for subsequent hydration. The embodiments of Bao have several disadvantages. First, the implant's size increases as it hydrates to its maximum volume. It is not feasible to precisely match the implant size to the desired intradiscal space (former nucleus), and therefore it cannot exert the optimum pressure on the vertebrae. In addition, during the hydration process, the core-containing jacket occupies a smaller space than the intradiscal space and is free to move around into a less favorable location while it is hydrating. Moreover, high pressure must be exerted on the implant in order to pass it through the insertion device. This process can release the implant at a high velocity into the intradiscal space and possibly damage the annulus.

U.S. Pat. No. 6,022,376 to Assell describes a capsule shaped prosthetic spinal disc nucleus for implantation into a human intradiscal space, made of a substantially inelastic constraining jacket surrounding an amorphous core. The jacket according to Assell is percutaneously implanted into a damaged disc space through a flap created in the annulus. The jacket can be implanted empty and then subsequently filled with the core through the use of a syringe or a catheter, which is directed to pass through the constraining jacket, or alternatively a core-containing jacket can be implanted. In both of these cases according to Assell, a final capsule volume is achieved following the hydration of the hydrogel core. Thus, like Bao, the teachings of Ansell have an inherent disadvantage of a small implant volume at the time of implantation that increases in volume over time. Further, the length of the flap according to Assell is about 12 millimeters and has a height of about 6 millimeters for use with a prosthetic body having a minor axis diameter of 7 millimeters. The relatively large size of the flap is an inherent and insurmountable drawback of the Assell device. Further, during the time that hydration takes place the core-containing jacket occupies a smaller space than in its final position and is free to move around into a less favorable position.

U.S. Pat. No. 6,306,177 to Felt describes the use of a curable polyurethane biomaterial composition adapted to be mixed at the time of use in order to provide a flowable composition and to initiate cure. Although the system according to Felt seemingly solves the problem of not completely filling up the available space, several drawbacks exist in Felt's system. These drawbacks include, among others, the unknown bio-stability of the thermoset polyurethane, the intricate instrumentation needed for the in-situ curing and the curing time which may be too rapid (less than a few minutes) for any last minute modifications.

U.S. Pat. No. 6,676,665 to Foley et al. describes instrumentation for treatment of the spine, including an elongate member having a deformable distal end portion at least partially formed of a flexible and preferably elastic material. The distal end portion has an initial configuration for placement adjacent a vertebral body and a deformed configuration defining at least one outwardly extending projection for displacement of at least a portion of the vertebral body. The elongate member preferably comprises a rod member, a sleeve member and an actuator mechanism for imparting relative linear displacement between the rod and sleeve members to effect outward deformation of the distal end portion of the sleeve member. In one embodiment, the instrumentation is used to compact cancellous bone to form a cavity within a vertebral body. In another embodiment, the instrumentation is used to reduce a compression fracture. In yet another embodiment, the instrumentation is used to distract a disc space between adjacent vertebral bodies.

Although many prosthetic disc devices are described in the literature, there is still a need for improvement in ease of manufacture and performance.

SUMMARY OF THE INVENTION

The present invention is directed to an elastomeric spinal disc nucleus replacement, as is described more in detail hereinbelow.

There is thus provided in accordance with an embodiment of the present invention a spinal disc nucleus replacement including an elastomeric sheath assembled around a rod, a portion of the sheath being arranged for sliding along the rod, and a sheath compactor adapted to slide a portion of the sheath along the rod from a first position to a second position, wherein in the first position the sheath is in a non-expanded orientation and in the second position the sheath is in an expanded orientation wherein folds of the sheath expand radially outwards from the rod.

The spinal disc nucleus replacement can include one or more of the following features. For example, a stopper may be at a distal portion of the rod and the sheath compactor may push a distal portion of the sheath against the stopper. A removable fastening ring may hold a portion of the sheath to the rod. The rod may include a removable portion. The rod may be flexible, and may be flexed into an arcuate shape. The rod may be constructed of a shape memory alloy or polymer, for example. The ends of the rod may be fastenable together. The rod may be withdrawn and removed from the sheath. The folds of the sheath may expand outwards generally uniformly or non-uniformly. The distance between folds of the sheath may vary axially along the rod. There may be more folds on one side of the sheath than on another side of the sheath. An anchor may be provided for attachment to spinal structure. A guiding wire may be provided for introducing the sheath thereover.

DESCRIPTION OF EMBODIMENTS

Figure 1:
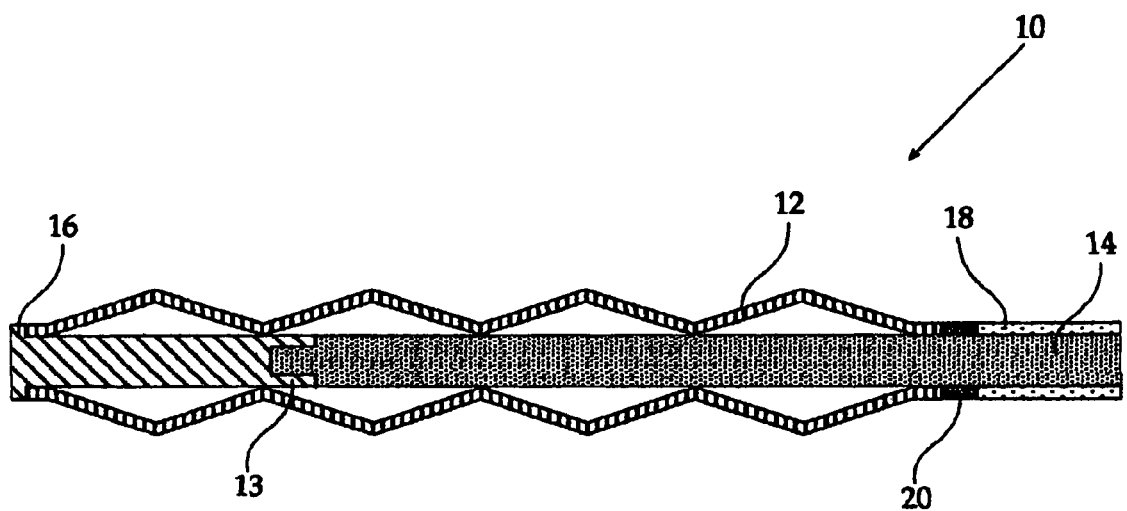
FIG. 1 is a cross sectional side view of one embodiment of the present invention in an uncompacted form, including a sheath disposed over a rod.

Reference is now made to FIG. 1, which illustrates an elastomeric prosthetic spinal disc nucleus implant 10 in its form prior to implantation, in accordance with an embodiment of the present invention. An elastomeric sheath 12, illustrated in its elongated form, may be assembled around an inner rod 14. Some non-limiting examples of elastomers suitable for constructing sheath 12 are polyurethane, latex, natural rubber, silicone rubber, nylon, and shape memory polymer. Rod 14 may be cylindrical in shape with a generally circular cross section, but the invention is not limited to this shape and rod 14 may have any other shape or cross section as well. A stopper 16 may be at or near one end of rod 14, attached to or integrally formed with sheath 12 and/or rod 14. Inner rod 14 and stopper 16 may be fashioned from any rigid material such as a hardened plastic or a metal and may have a unitary (i.e., one-piece) construction or may be constructed of a plurality of parts joined by one or more junctures 13.

A sheath compactor 18 may be used to compact sheath 12 from a first elongated and narrow form to a second compacted and thicker form wherein sheath 12 is compacted toward stopper 16. The implant 10 in its elongated form is configured to enter a small hole (for example, 6 mm or less in diameter) and can expand subcutaneously to a diameter greater than the entry hole.

Before compacting, the maximum thickness of the sheath is much thinner than after compacting, which allows for a minimal invasive procedure and enabling the procedure to be performed with a standard instrument set for percutaneous spine surgery.

A fastening ring 20 may be used to hold sheath 12 before and/or after compression by compactor 18.

Figure 2:
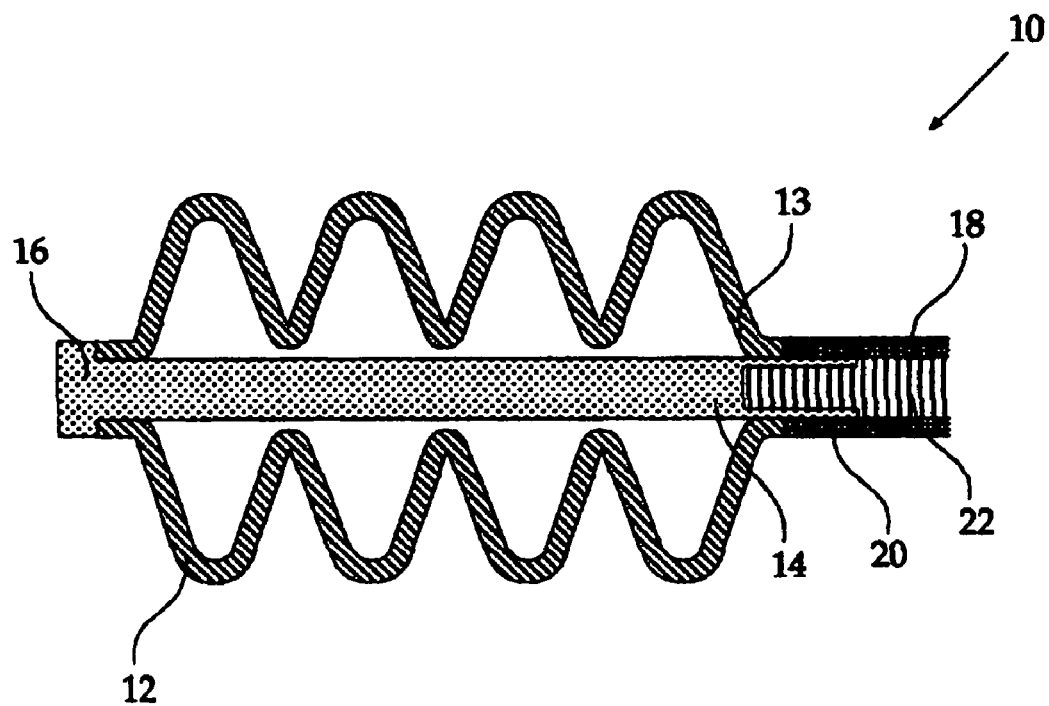
FIG. 2 is a cross sectional side view of the embodiment of FIG. 1 in a compacted form (that is, the sheath is in an expanded orientation and compacted along the length of the rod) prior to removal of an exposed medial rod.

Reference is now made to FIG. 2, which illustrates the elastomeric containing prosthetic spinal disc nucleus implant 10 after expansion to the expanded orientation, for insertion into place within the intra-discal space (not shown). The sheath compactor 18 has been moved further down inner rod 14 toward stopper 16 (i.e., to the left in the sense of the illustration). Folds of sheath 12 bulge outwards in the expanded orientation in an accordion-like manner. The amount the folds of sheath 12 bulge outwards is a function of the final position of sheath compactor 18. This position of sheath compactor 18 may be predetermined before the procedure by using radiological or other means, for example. Sheath compactor 18 may be first detached from fastening ring 20 in order to move it along rod 14. Afterwards, fastening ring 20 may be re-attached at the final position on inner rod 14 by any one of numerous means including a catch and a ratchet, snap, thread, etc.

Figure 3:
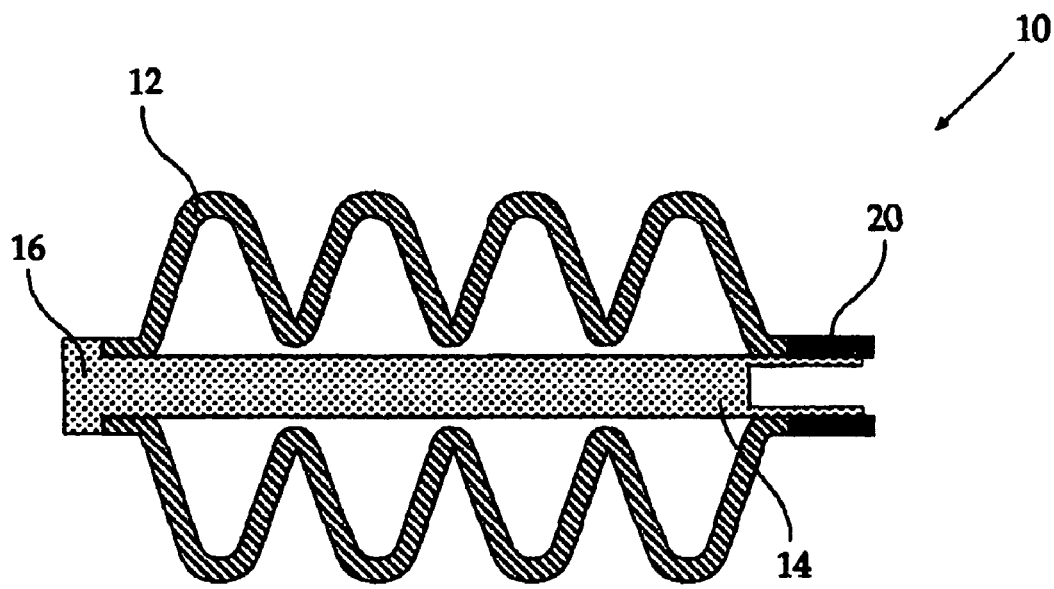
FIG. 3 is a cross sectional side view of the embodiment of FIG. 1 in the compacted form following the removal of the exposed medial rod.

A portion 22 of inner rod 14 that may be uncovered or exposed by sheath 12 may now be separated (detached and removed) from the implant 10, such as by breaking it off the rest of inner rod 14 or by unscrewing portion 22 at any one of a number of predetermined places such as at juncture 13, as seen in FIG. 3.

Figure 4:
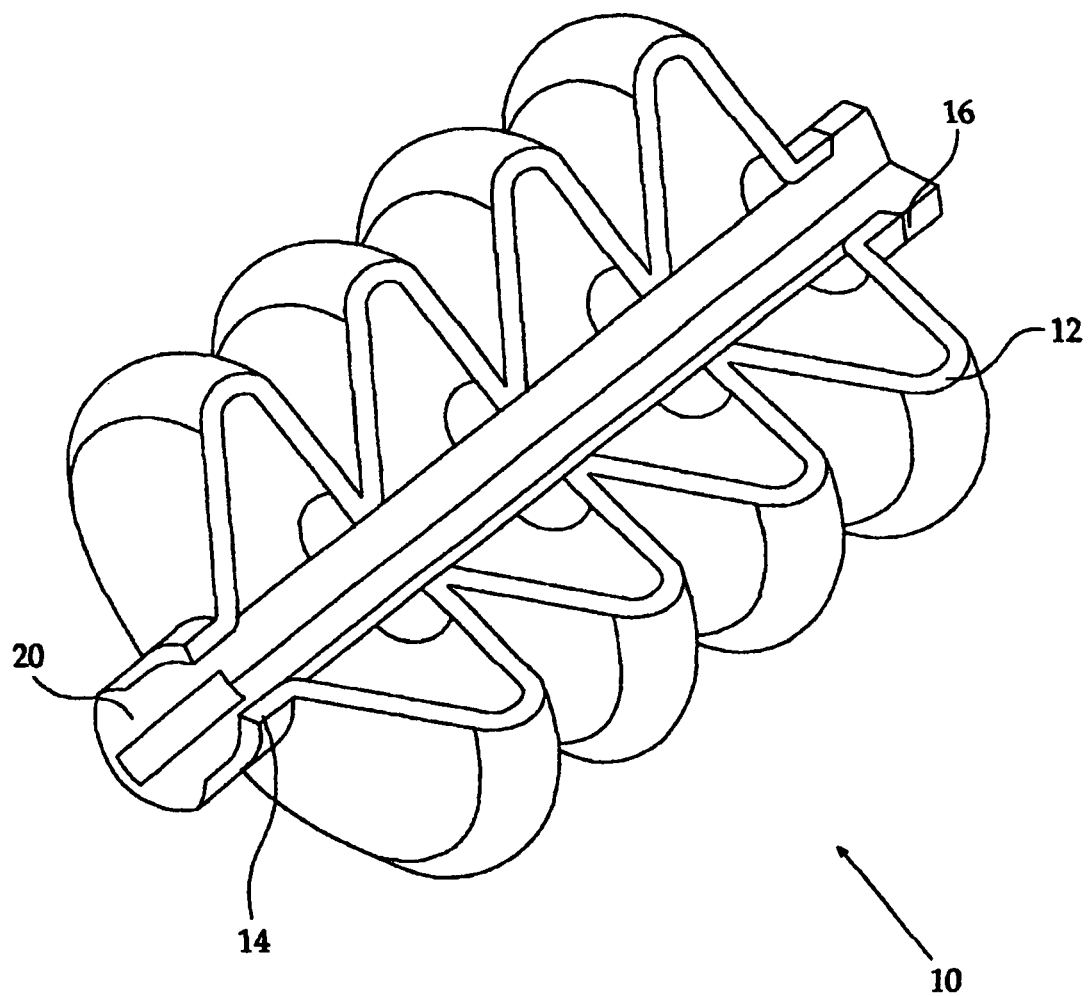
FIG. 4 is a perspective cut away view of one embodiment of an elastomeric prosthetic spinal disc nucleus implant according to the present invention.

FIG. 4 is a perspective cut-away view of elastomeric prosthetic spinal disc nucleus implant 10 illustrated in its final compacted form.

Figure 5:
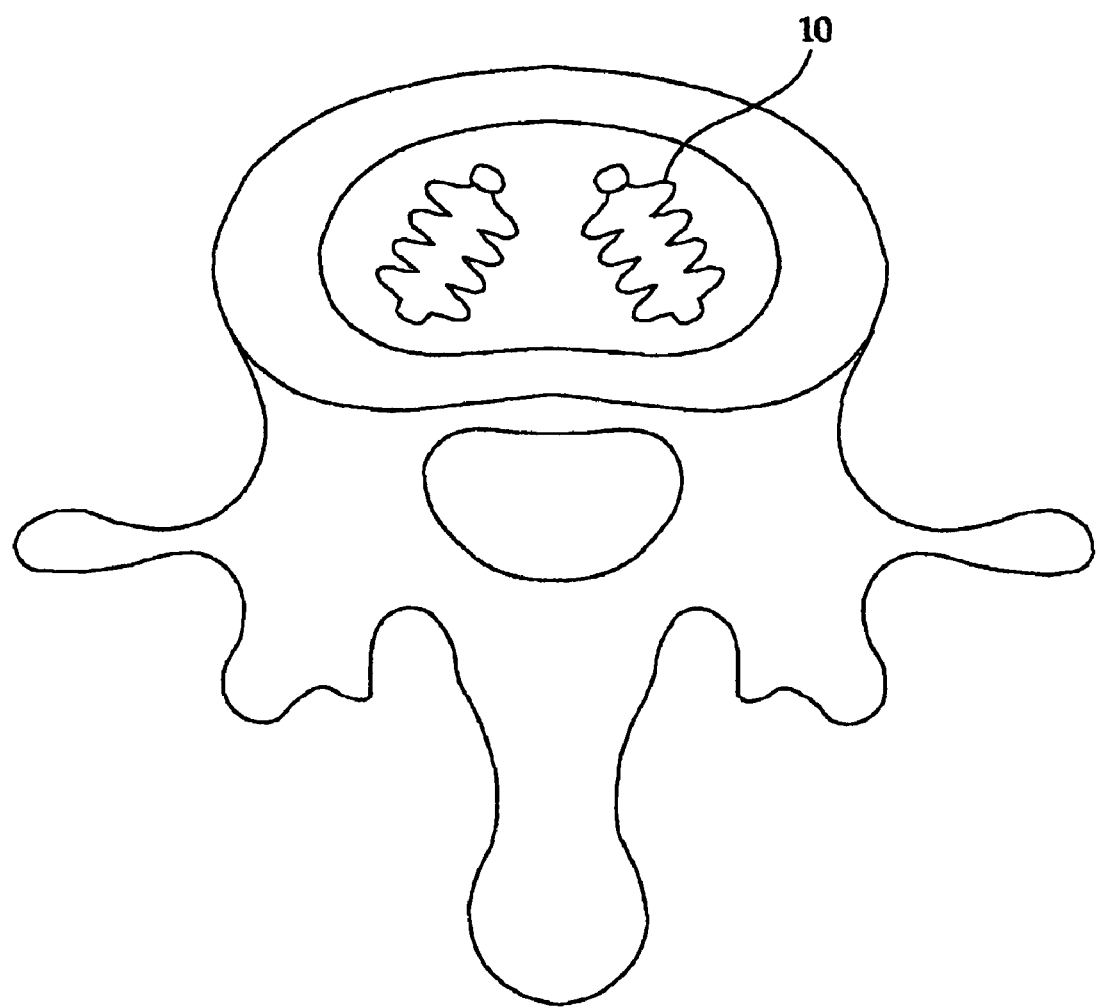
FIG. 5 is a cross-sectional view of an intra-discal space showing two compacted elastomeric prosthetic spinal disc nucleus implants according to the present invention in situ.

FIG. 5 is a cross-sectional view of an intra-discal space showing two compacted elastomeric prosthetic spinal disc nucleus implants 10 in situ.

Figure 6:
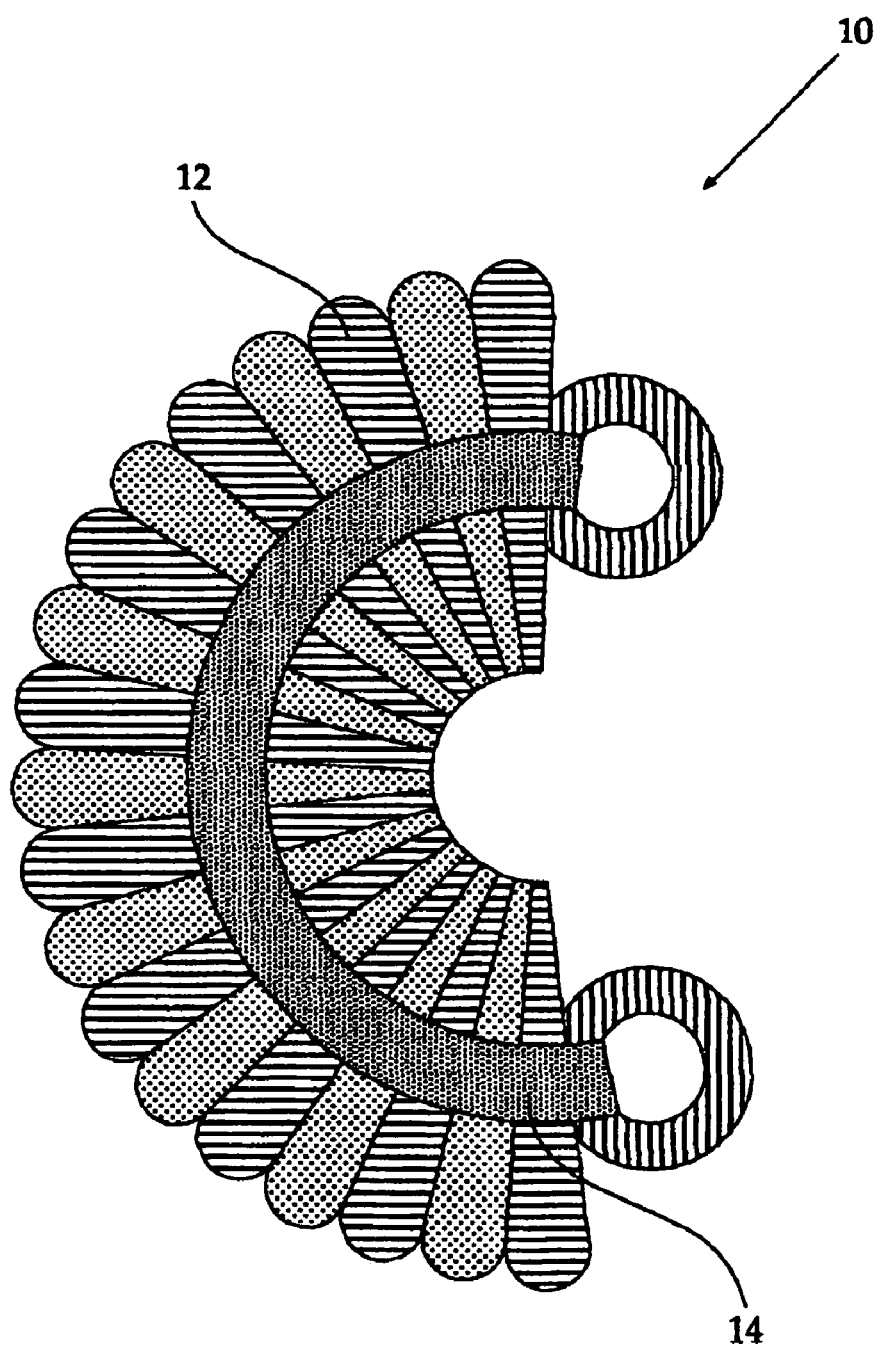
FIG. 6 is a cross sectional side view of an additional embodiment of the present invention featuring a medial rod with shape memory in the compacted form following the removal of the exposed medial rod.
Figure 7:
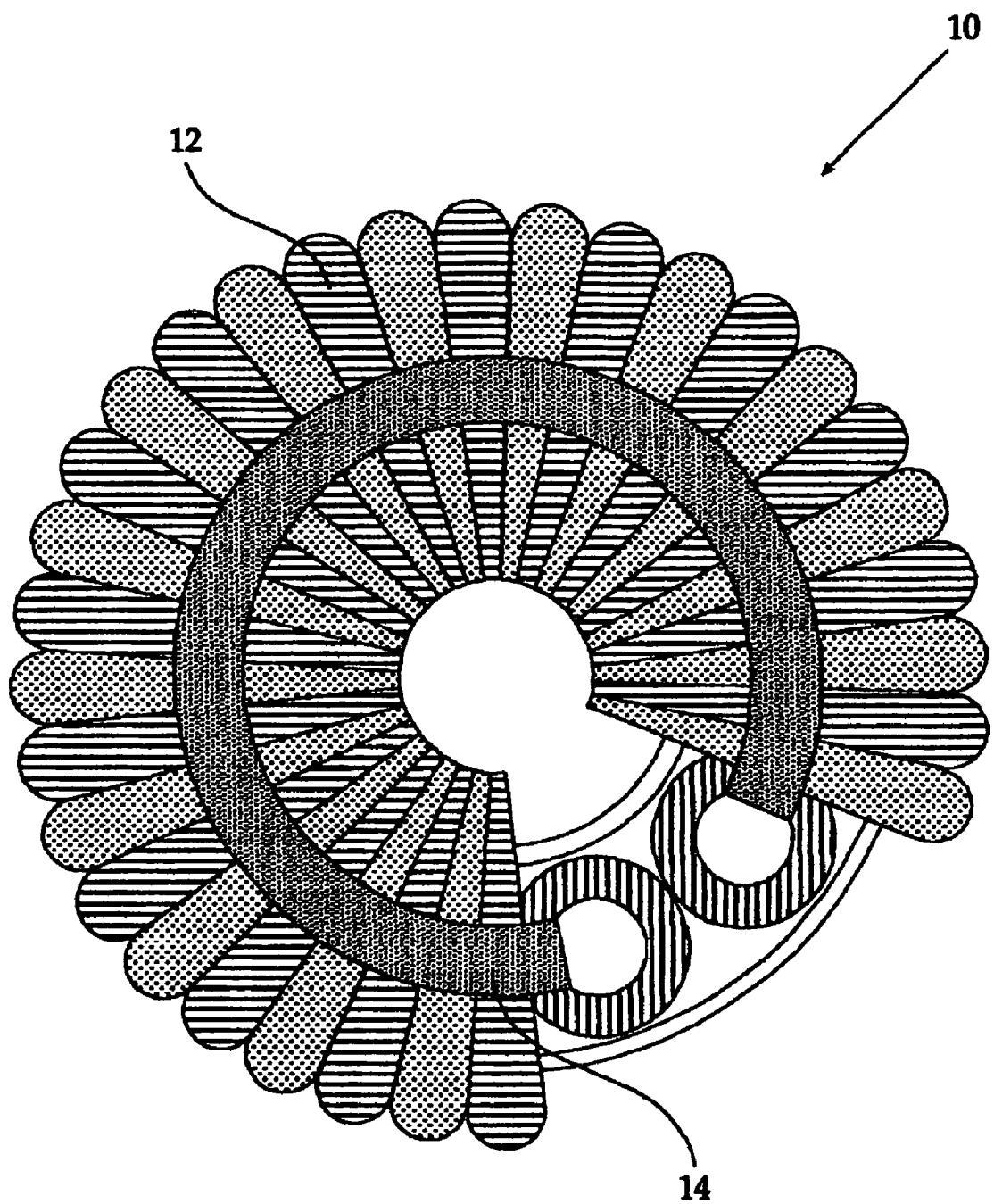
FIG. 7 is a cross sectional side view of yet another embodiment of the present invention featuring a medial rod with shape memory in the compacted form following the removal of the exposed medial rod.

According to some embodiments of the invention, rod 14 may be flexible. In such an embodiment, rod 14 may be constructed, without limitation, from a flexible plastic (e.g., polyurethane, nylon, shape memory polymer) or flexible metal (e.g., stainless steel, shape memory alloy such as NITINOL), and may be constructed similarly to catheters and guide wires used in angioplasty. This allows implant 10 to assume a curved configuration such as, for example arcuate (FIG. 6) or circular (FIG. 7). These embodiments are expected to find utility in a variety of medical applications including, but not limited to, spinal disc nucleus replacement and meniscus replacement or in other places where it is necessary to replace or add tissue with the additional advantage of the cushioning affect of the elastomeric sheath 12.

In an embodiment wherein rod 14 is constructed from a shape memory alloy or polymer, rod 14 may be held in a straight configuration by an external force and assume the desired curved configuration when the external force is removed. The required external force may be supplied, for example, by a removable rigid core within rod 14 or by a rigid tube which contains rod 14 and sheath 12. In such a flexible embodiment, two ends of rod 14 may be fastened together (with any suitable fastener, such as but not limited to, screws, clips, snaps, bonding, sonic welding, VELCRO and the like) in order to retain a shape.

In accordance with a further embodiment of the invention, the inner rod 14 may be used for guiding sheath 12 to the intra-discal space, and may be withdrawn and removed from the intra-discal space following expansion of sheath 12.

In the illustrated embodiment, the folds of sheath 12 expand outwards generally uniformly. However, the invention also encompasses non-uniform expansion, which may be achieved by varying the distance between folds in sheath 12 axially along rod 14 (that is, axially different spacing of the folds), or alternatively, by varying the number of folds in sheath 12 on different sides of rod 14 (that is, radially different spacing of the folds).

Combinations of axial and radial differentiation, in combination with flexible rods 14, enable producing virtually any shape of implant 10, whether symmetric or asymmetric.

Figure 8:
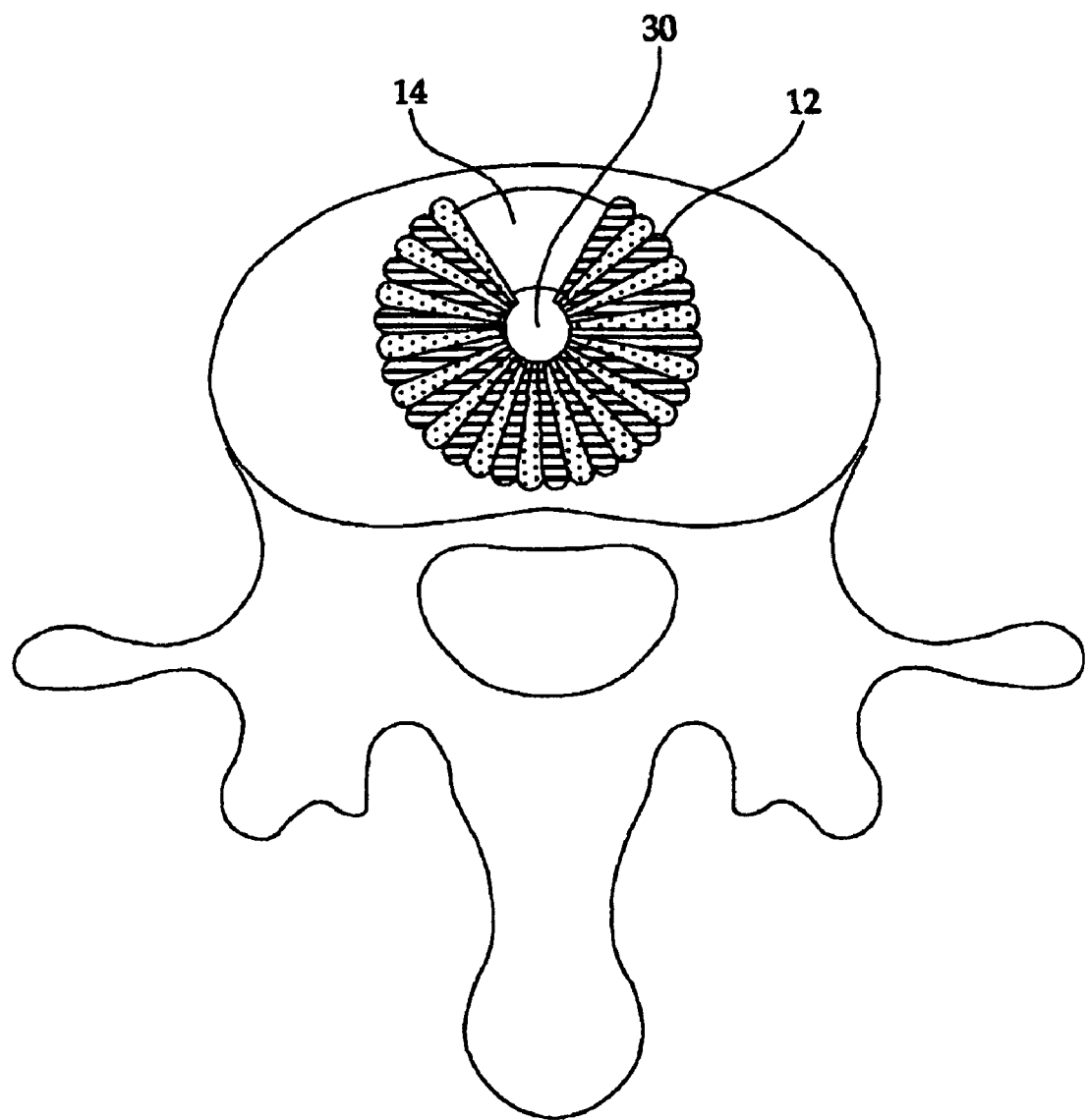
FIG. 8 is a view of an intra-discal space showing a compacted elastomeric prosthetic spinal disc nucleus implant featuring a medial rod with shape memory according to the present invention in situ.

FIG. 8 is a cross-sectional view of an intra discal space 30 showing a compacted elastomeric prosthetic spinal disc nucleus implant featuring sheath 12 on a medial rod 14 with tensile memory in situ.

Figure 9:
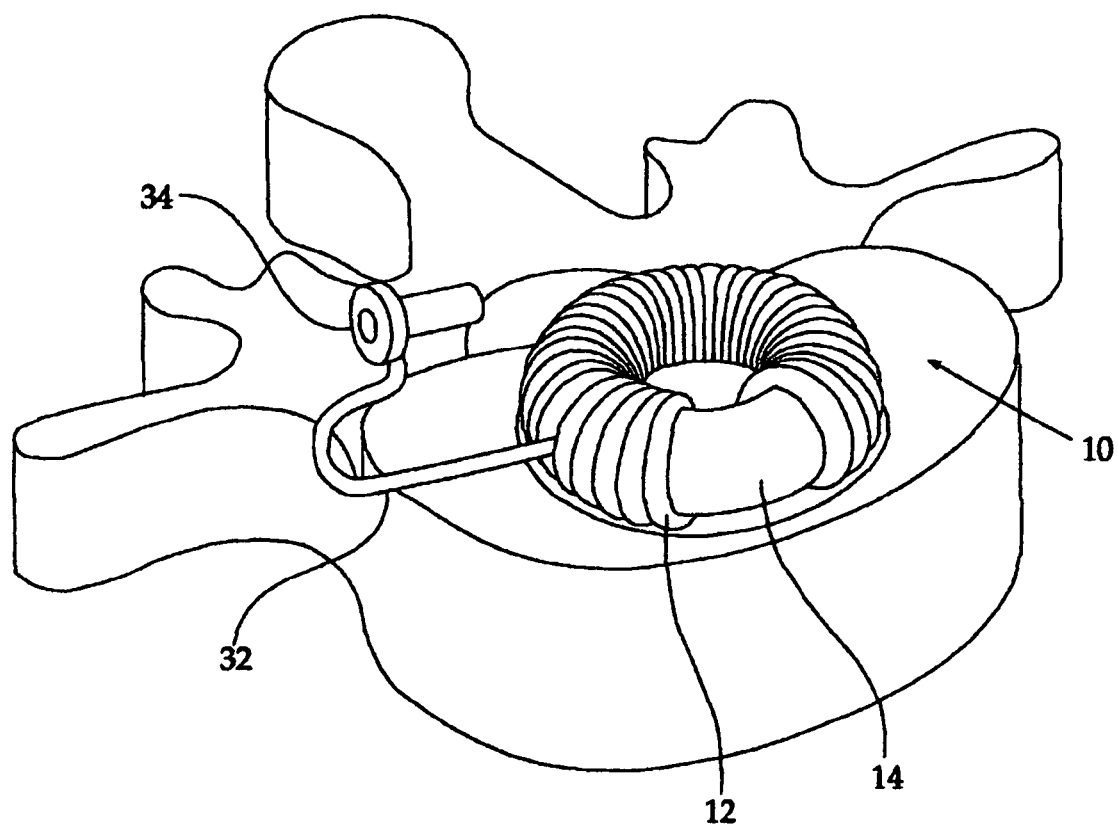
FIG. 9 is a top view of the implant of FIG. 8 shown in place in a disc space with the adjacent vertebra removed for the illustration.

According to some embodiments of the invention, implant 10 may be attached or anchored into one of the adjacent vertebral bones. This may help in keeping implant 10 in place and prevent any dislodgement or movement. Such an embodiment is illustrated in FIG. 9, which is a top view of implant 10 shown in place in a disc space with the adjacent vertebra removed for the illustration. An anchor 32 may be integrally formed with implant 10 or alternatively attached to implant 10 at one end either before or after the implant is attached to an adjacent vertebra. Attachment may be accomplished by means of one or more fasteners 34, such as but not limited to, screws, rivets, bolts and the like.

Figure 10:
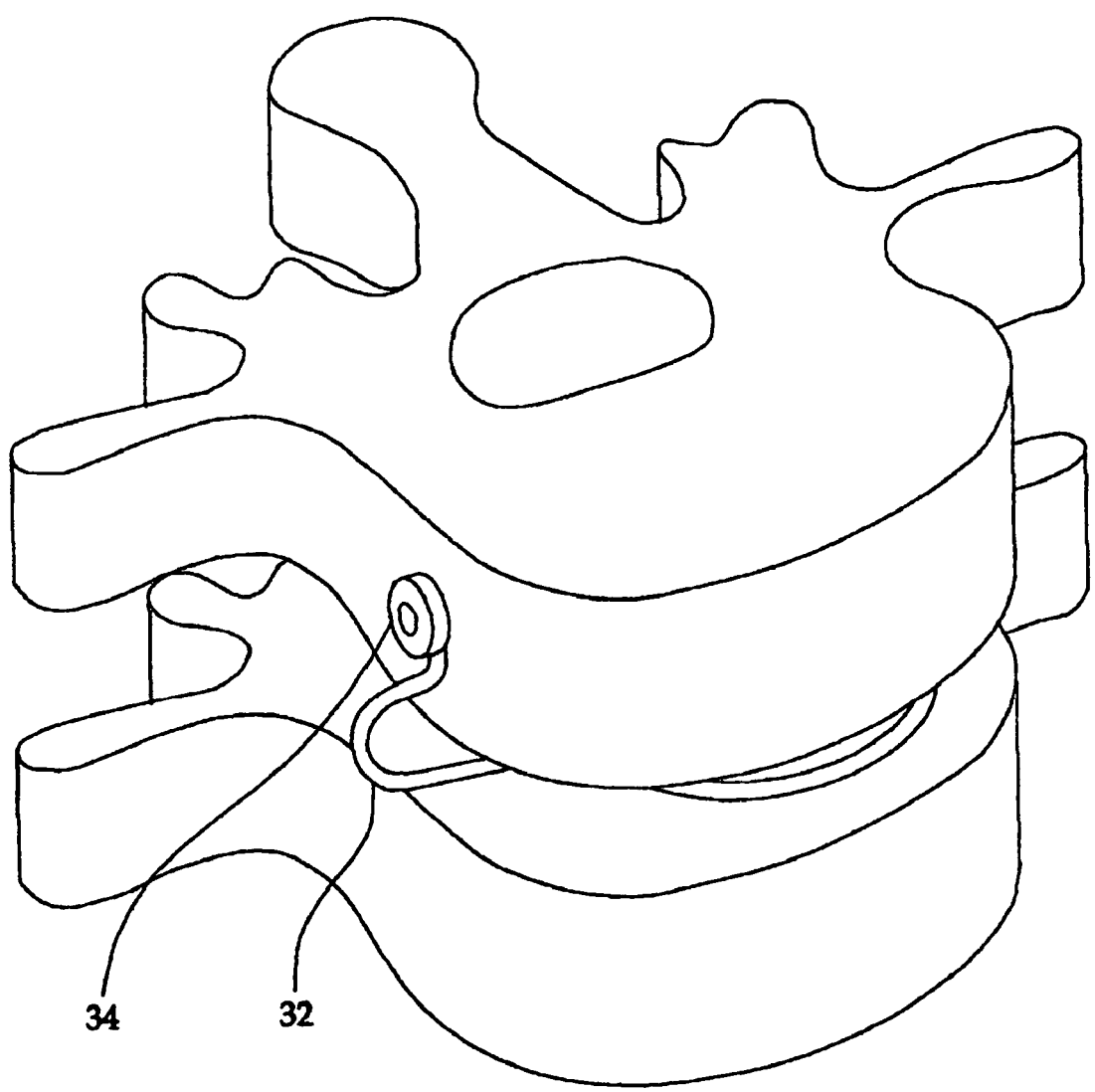
FIG. 10 is a top view of the implant of FIG. 8 shown in place in a disc space with the adjacent vertebra in place for the illustration.
Figure 11:
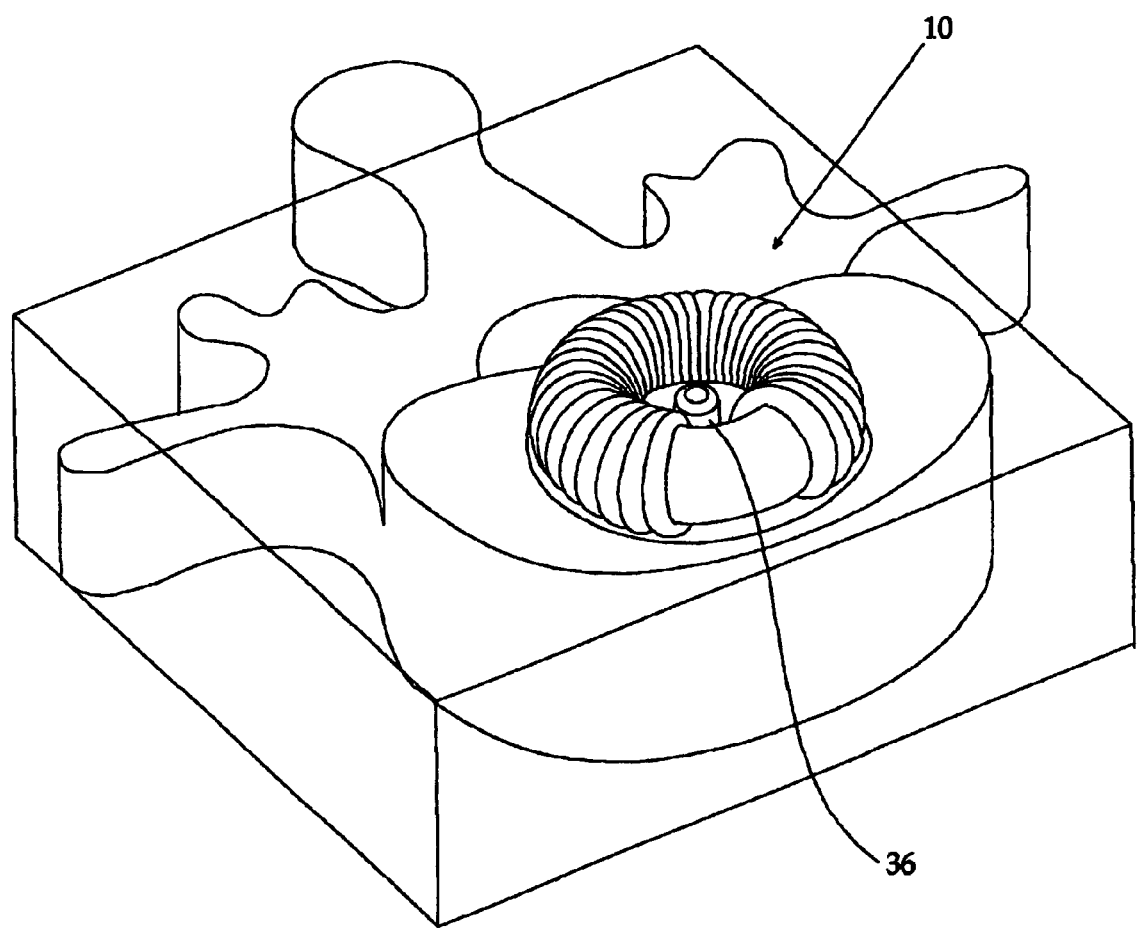
FIG. 11 is a view of an embodiment of the invention in which an anchor is fastened into an endplate.

FIG. 10 is a top view of implant 10 shown in place in a disc space and attached or anchored into one of the adjacent vertebral bones with fastener 34. FIG. 11 illustrates another embodiment of the invention, in which an anchor 36 may be anchored into the vertebral bone through the endplate of at least one of the adjacent vertebrae either prior to or after implant 10 has been placed.

Figure 12:
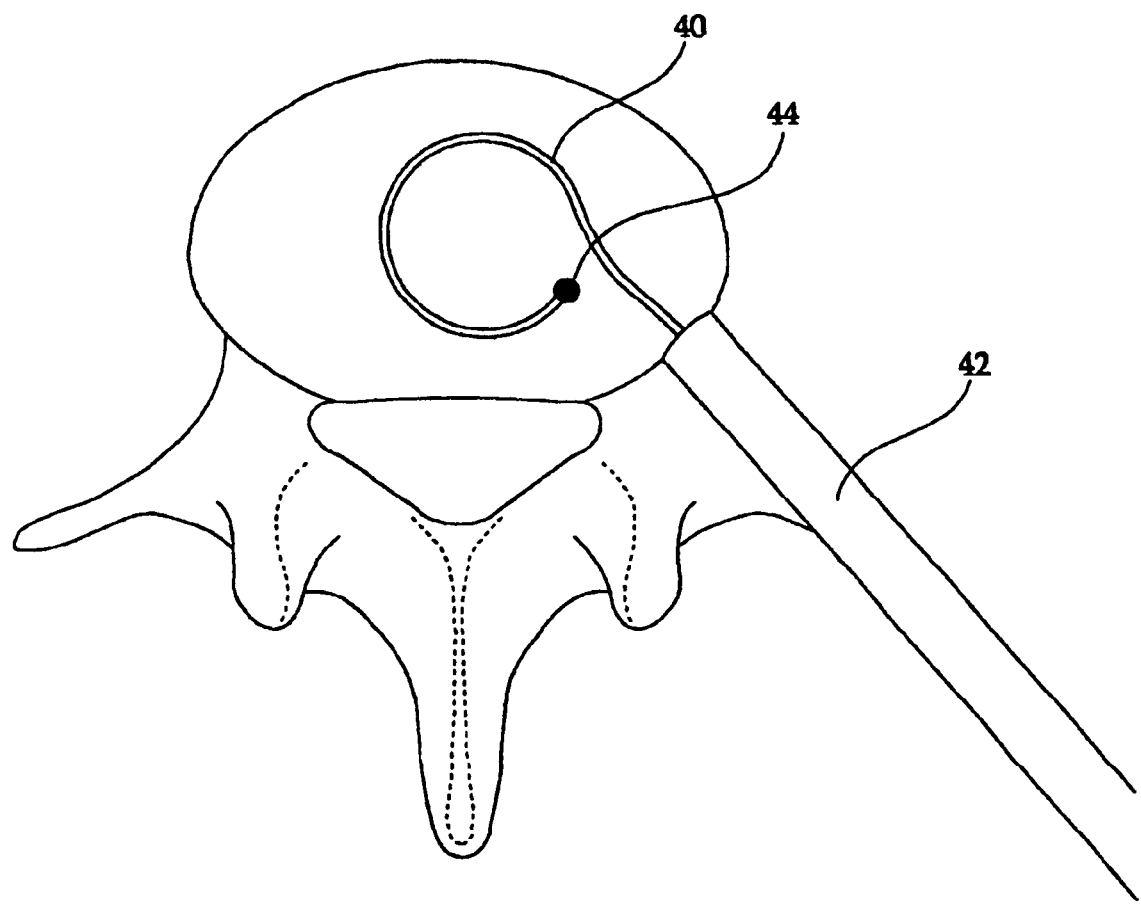
FIG. 12 is a top view of an embodiment of the invention in which a sheath is introduced over a guiding wire.
Figure 13:
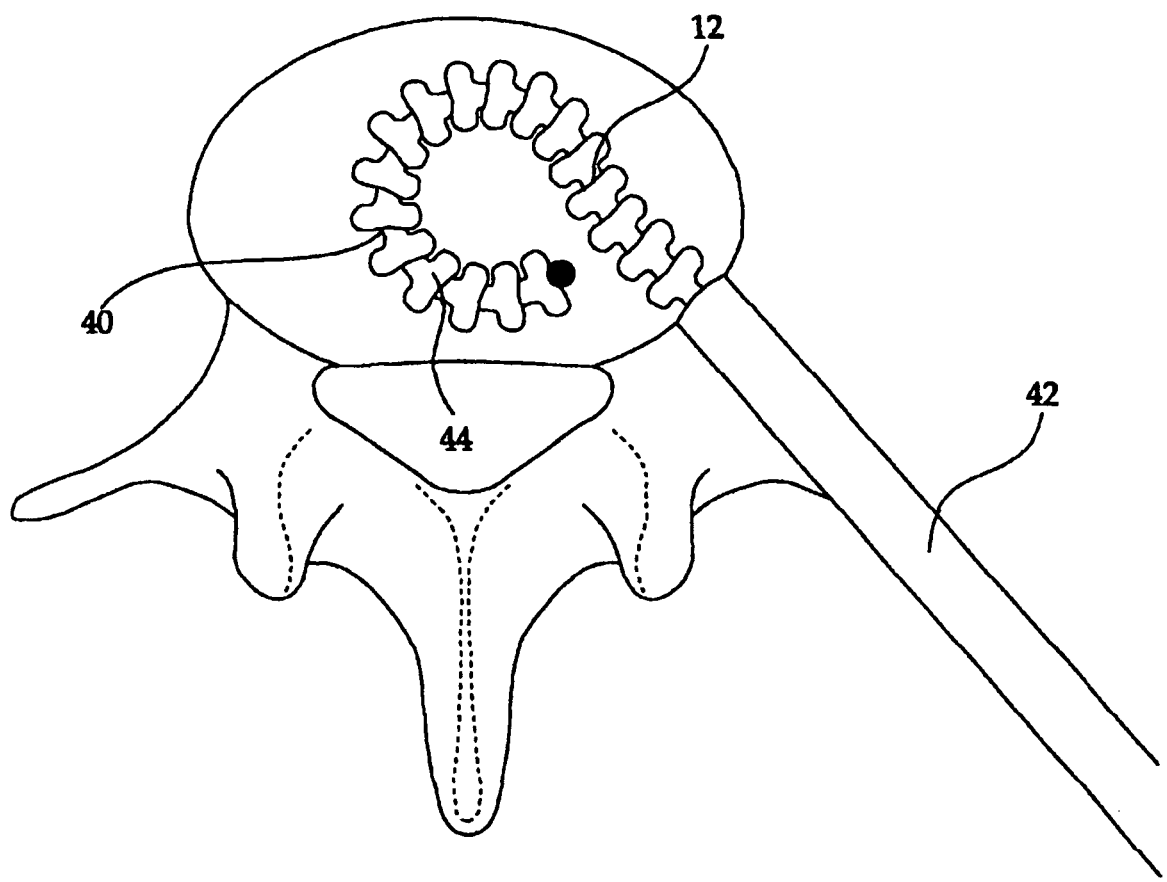
FIG. 13 is another top view of an embodiment of the invention in which a sheath is introduced over a guiding wire in which the sheath is progressing down the guiding wire.

Reference is now made to FIGS. 12 and 13, which illustrate an embodiment of the invention in which sheath 12 is introduced over a guiding wire 40. The guiding wire 40 may be first placed in the intra-discal space as illustrated in FIG. 12. The guiding wire 40 may be made of shape memory metal rod, and may be arcuate or circular when released into the intra-discal space. An applicator 42 may be used to introduce either or both of the guiding wire 40 or the sheath 12 into the intra-discal space prior to expanding sheath 12. After the guiding wire 40 is in place, implant 10 may be fed into the intra-discal space over the guiding wire 40 in an uncompacted form (that is, contracted, non-expanded orientation) and then may be compacted to a thicker form, as described hereinabove. A stopper 44 may be placed at the end of the guiding wire 40 that will stop the sheath 12 from progressing further than the length of the guiding wire 40. FIG. 13 illustrates the embodiment as illustrated in FIG. 12 showing the sheath 12 approximately over half way down the guiding wire 40 in a direction towards the stopper 44. After sheath 12 reaches stopper 44, guiding wire 40 may be tethered so that sheath may be compacted on guiding wire 40 in a direction towards stopper 44, as described hereinabove. Inner rod 14 may be hollow in order to accommodate guide wire 40.

Although the invention has been described in conjunction with specific embodiments thereof, it is evident that many alternatives, modifications and variations will be apparent to those skilled in the art. Accordingly, it is intended to embrace all such alternatives, modifications and variations.

What is claimed:

1. A spinal disc nucleus replacement comprising:
    an elastomeric sheath surrounding an outside portion of a flexible rod having opposite ends, a portion of said sheath being arranged for sliding along said rod; and
    a sheath compactor adapted to slide a portion of said sheath along said rod from a first position to a second position, wherein the second position is more distal into a patient than the first position, wherein in the first position said sheath is in a non-expanded orientation and in the second position said sheath is in an expanded orientation wherein folds of said sheath expand radially outwards from said outside portion of said rod, wherein said elastomeric sheath surrounds the outside portion of the rod both in the non-expanded and expanded orientations and wherein said folds in the expanded orientation comprise a plurality of crests and troughs wherein said rod is flexed into an arcuate shape, and wherein the opposite ends of said rod are fastened together to retain said accurate shape.

2. The spinal disc nucleus replacement according to claim 1, wherein a stopper is at a distal portion of said rod and said sheath compactor is adapted to push a distal portion of said sheath against said stopper.

3. The spinal disc nucleus replacement according to claim 1, wherein a removable fastening ring holds a portion of said sheath to said rod.

4. The spinal disc nucleus replacement according to claim 1, wherein said rod comprises a removable portion.

5. The spinal disc nucleus replacement according to claim 1, wherein said rod is constructed of at least one of a shape memory alloy and a shape memory polymer.

6. The spinal disc nucleus replacement according to claim 1, wherein said rod is withdrawable and removable from said sheath.

7. The spinal disc nucleus replacement according to claim 1, wherein said folds of said sheath expand outwards generally uniformly.

8. The spinal disc nucleus replacement according to claim 1, wherein said folds of said sheath expand outwards non-uniformly.

9. The spinal disc nucleus replacement according to claim 1, wherein a distance between folds of said sheath varies axially along said rod.

10. The spinal disc nucleus replacement according to claim 1, wherein there are more folds on one side of said sheath than on another side of said sheath.

11. The spinal disc nucleus replacement according to claim 1, further comprising an anchor for attachment to spinal structure.

12. The spinal disc nucleus replacement according to claim 1, further comprising a guiding wire for introducing said sheath thereover.

13. The spinal disc nucleus replacement according to claim 12, further comprising another stopper placed at an end of said guiding wire that stops said sheath from progressing further than a length of said guiding wire.

14. The spinal disc nucleus replacement according to claim 1, wherein said sheath is constructed of at least one of polyurethane, latex, natural rubber, silicone rubber, nylon, and shape memory polymer.

15. The spinal disc nucleus replacement according to claim 1, wherein said troughs of said elastomeric sheath are adjacent said rod.

16. The spinal disc nucleus replacement according to claim 1, wherein said folds of said sheath are spaced generally equally from each other.

* * * * *